US011638822B2

(12) United States Patent
Thorne et al.

(10) Patent No.: US 11,638,822 B2
(45) Date of Patent: May 2, 2023

(54) ELECTRICAL NERVE STIMULATOR

(71) Applicant: Arctoro Medical, LLC, Logan, UT (US)

(72) Inventors: Steven Thorne, Logan, UT (US); William Hatch, Logan, UT (US); Ryan Lindsley, Logan, UT (US)

(73) Assignee: ARCTORO MEDICAL, LLC, Logan, UT (US)

( * ) Notice: Subject to any disclaimer, the term of this patent is extended or adjusted under 35 U.S.C. 154(b) by 105 days.

(21) Appl. No.: 16/920,010

(22) Filed: Jul. 2, 2020

(65) Prior Publication Data
US 2021/0001120 A1    Jan. 7, 2021

Related U.S. Application Data

(60) Provisional application No. 62/869,870, filed on Jul. 2, 2019.

(51) Int. Cl.
| *A61N 1/18* | (2006.01) |
| *A61N 1/36* | (2006.01) |
| *G06F 3/04847* | (2022.01) |
| *A61N 1/04* | (2006.01) |
| *G06F 3/14* | (2006.01) |

(52) U.S. Cl.
CPC ....... *A61N 1/36021* (2013.01); *A61N 1/0456* (2013.01); *A61N 1/36034* (2017.08); *G06F 3/04847* (2013.01); *G06F 3/14* (2013.01)

(58) Field of Classification Search
CPC ............ A61N 1/36021; A61N 1/36034; A61N 1/0456; G06F 3/04847
See application file for complete search history.

(56) References Cited

U.S. PATENT DOCUMENTS

| 5,470,349 A | * | 11/1995 | Kleditsch | ............. | A61N 1/0452 |
| | | | | | 607/150 |
| 2016/0310734 A1 | * | 10/2016 | Nodskov | .............. | A61N 1/0476 |

* cited by examiner

*Primary Examiner* — Alyssa M Alter
(74) *Attorney, Agent, or Firm* — Travis Banta; Loyal IP Law, PLLC

(57) ABSTRACT

This disclosure generally relates to a device, method, and system for diagnosing and treating nerve injuries with electrical stimulation. A probe is provided which connects to a nerve stimulator system which measures voltage and electrical current applied to a living body to detect a nerve injury location. A processor within the nerve stimulator system may adjust the voltage and current output to numb or deaden an injured nerve.

10 Claims, 5 Drawing Sheets

ELECTRICAL NERVE STIMULATOR

CROSS-REFERENCE TO RELATED APPLICATIONS

This application claims the benefit of U.S. Provisional Application No. 62/869,870, filed Jul. 2, 2019, which is hereby incorporated by reference herein in its entirety, including but not limited to those portions that specifically appear hereinafter, the incorporation by reference being made with the following exception: In the event that any portion of the above-referenced provisional application is inconsistent with this application, this application supersedes said above-referenced provisional application.

BACKGROUND

1. Technical Field

This disclosure relates generally to a system, method, and device for treating nerve injuries and nerve impingements in living bodies. A probe may be used to test nerves which may be causing pain. A probe may be moved along an area of a living body experiencing pain. When a spike in electrical current is identified, a point along a nerve where injury or impingement has occurred may be identified as the source of pain. The probe may then apply an electrical current to the nerve and reduce or eliminate pain caused by the detected nerve

2. Description of the Related Art

Pain and pain management have long afflicted humans on earth, likely from the earliest days of antiquity. Since pain is unpleasant, mankind has sought ways to minimize the effect of pain caused by an injury or age. In some cases, devices, like shoes for example, were created as a preventative measure to minimize potential injury by covering a user's foot to prevent splinters, rocks, or falling objects from causing pain or irreparable damage. Medicines were also developed to reduce a brain's sensitivity to pain, making the pain more tolerable. At first, these medicines were extracts or natural chemicals that were assembled by naturalists familiar with the effects of certain plant and animal extracts on living bodies. Some of these medicines contained actual medicinal benefit while other medicines operated solely based on a placebo effect.

In addition to devices and medicine, mankind has also developed the capability of performing surgery on living bodies. Surgery from antiquity to modern times was more butchery than surgery because of the lack of tools or sophisticated analysis tools to tell a surgeon, who was more likely a barber, what problems existed within the body before cutting the body open occurred. Many people with simple painful ailments by today's standards died on tables in the hands of minimally skilled medical practitioners.

In modern times, mankind has increased its ability to harness the chemical effects of certain medicines on living bodies with better processes to extract medicinal materials from natural sources or to synthesize medicinal materials in a laboratory environment. However, these medicines can be addictive and limit users' ability to think clearly and rationally.

Likewise, the use of non-invasive tools, such as X-rays, ultrasound technology, magnetic resonance imaging technology, CT scan technology, and a host of others have made surgery much safer than it has historically been. However, living bodies remain as complicated as they ever have been and, still, certain surgeries can be extremely high risk for death, paralysis, or other side effects. One problem area for surgery in living bodies has been the spine and surrounding area. Because living bodies tend to have significant nerve activity in the spinal area, surgeons typically will operate on spinal problems as a last resort. Even minor cuts in the spinal area can result in drastic injury to a patient, making surgery undesirable if at all avoidable.

Accordingly, other non-invasive devices have been developed to reduce nerve pain, especially in, but not limited to, the spinal area. One such example is a so called "TENS" (transcutaneous electrical nerve stimulation) device. TENS devices provide a low-voltage electric current to a pad attached to the skin of a person experiencing pain. In the context of a spinal injury, a plurality of TENS pads is applied to the skin in the general area of the pain on the living body. Electrical stimulation is applied to the skin through the pads which causes the underlying nerves to be confused by the electrical stimulation. The nerves in the broad area are over sensitized to the effect of the electrical stimulation and cease to provide pain indications to the brain of the living body. Essentially, the TENS device has a numbing effect that provides short term pain relief to the living body. In this case, TENS devices can provide relief to a living body for 10 minutes to an hour, depending on severity of the pain, intensity of the electrical stimulation, and a host of other factors.

Unfortunately, TENS devices have limited usefulness because the pain relief is so short and takes 10-20 minutes to apply the electrical stimulation over a broad area of the living body. While the relief is welcome, being unable to resume pain free function for an hour is little comfort, which typically drives afflicted people back to an ice pack for relief. Accordingly, a need exists for better pain management for nerve injuries and impingements.

It is one object of this disclosure to provide a system which identifies a source of pain and targets a particular nerve causing the pain for correction. It is another object of this disclosure to provide a device which may apply an electrical current to a nerve identified as causing pain. It is another object of this disclosure provide a method for treating an injured or impinged nerve.

SUMMARY

Disclosed herein is a system. The system includes a probe and a graphical user interface. The probe applies an electrical current to a nerve in a living body. The graphical user interface identifies a location of injury or impingement of a nerve in the living body.

Also disclosed herein is a device which applies electrical current to a nerve. The device may include a tip, a casing, and a switch for selectively applying electrical current to a selected nerve by the tip.

Further disclosed herein, is a method for treating a nerve in a living body. The nerve may be identified using a probe and a graphical user interface by detecting an injured or impinged nerve, detecting the location of the injured or impinged nerve, and applying an electrical current by the probe to the detected location of the injured or impinged nerve.

BRIEF DESCRIPTION OF THE DRAWINGS

The accompanying drawings illustrate various embodiments of an electrical nerve stimulator system, method, and device disclosed herein.

DETAILED DESCRIPTION OF PREFERRED EMBODIMENTS

In the following description, for purposes of explanation and not limitation, specific techniques and embodiments are set forth, such as particular techniques and configurations, in order to provide a thorough understanding of the device disclosed herein. While the techniques and embodiments will primarily be described in context with the accompanying drawings, those skilled in the art will further appreciate that the techniques and embodiments may also be practiced in other similar devices.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
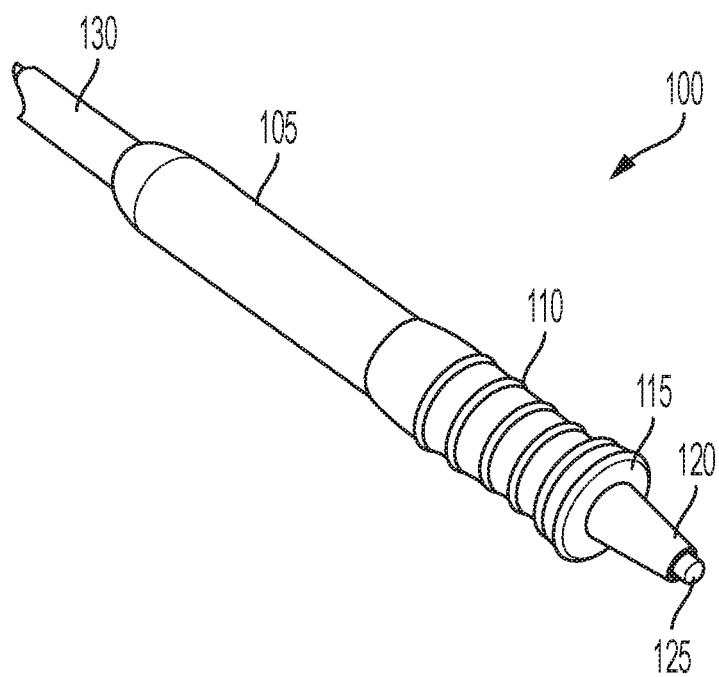
FIG. 1 illustrates an exemplary probe device.

FIG. 1 illustrates an exemplary probe 100 which is used to both electrically test nerve injuries and nerve impingements in a living body. Probe 100 may be used on any living creature including animals and humans to treat nerve injuries. As used herein the term "nerve injuries" may be broadly construed and may mean any damage or undesirable condition of a nerve, such as a pinched nerve, a severed nerve, or damaged nerve cluster and may include nerve impingements. Typically, probe 100 may be connected to a testing unit, which will be discussed below. The testing unit may further provide a connection for an electrical patch which is applied to skin of a living body. For purposes here, the terms "person" and "living body" may be interchangeable. While it is anticipated that most applications for the electrical nerve stimulator disclosed herein will be used on living persons, it is also possible that the electrical nerve stimulator disclosed herein may also find application in veterinary medicine. Thus, the term "person" is not intended to exclude the use of the electrical nerve stimulator disclosed herein on animals of any suitable physiology.

Probe 100 may include a casing 105 that acts as a body of probe 100. Casing 105 may be fitted with a handle 110 which may assist a practitioner in holding and using probe 100. Casing 110 may end at tip 115 which provides a cone 120 to an electrical stimulator 125 disposed in tip 115 at a top of cone 120. Electrical stimulator 125 may be made using any conductive material. One preferred embodiment for implementing electrical stimulator 125 may be using copper as electrical stimulator 125. Probe 100 may further be connected to a cable 130, which is connected to a testing unit, which will be disclosed below.

In practice, probe 100 may be used to complete an electrical circuit through a living body and measure the voltage, current, and resistance between different locations on the living body. As probe 100 is moved to come into transcutaneous contact with a nerve in the living body, voltage and current may be detected which identifies a location of a specific nerve. A person may identify that nerve as being one that is causing pain. A further explanation of probe 100 will be discussed below relative to other views of probe 100.

Figure 2:
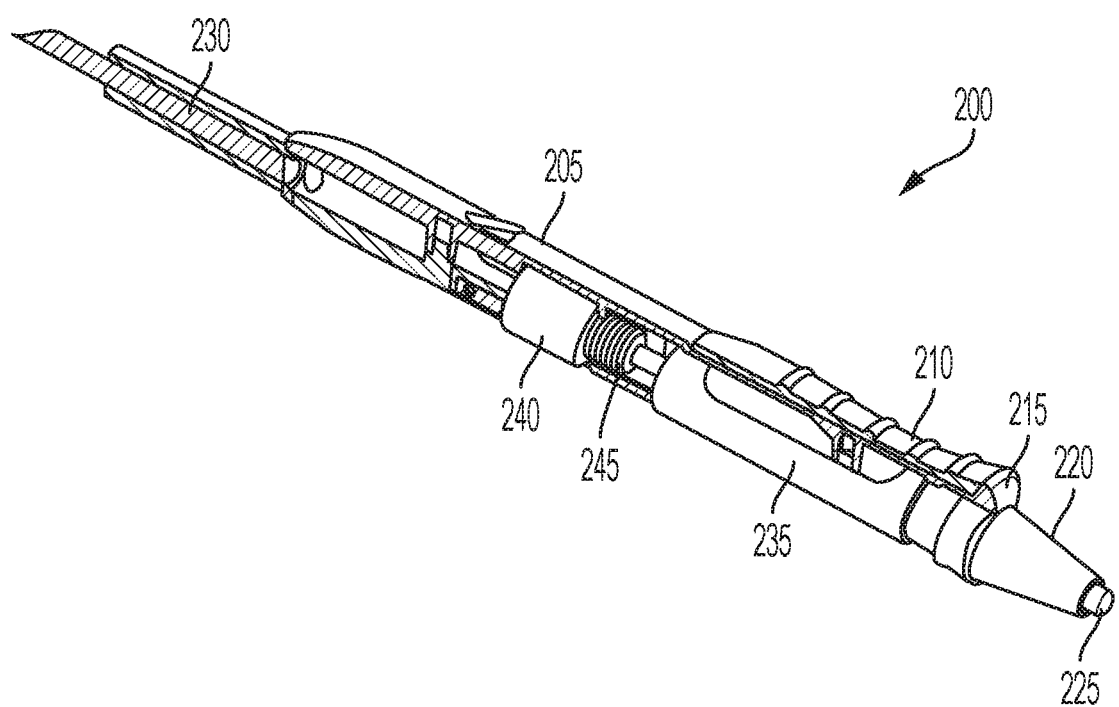
FIG. 2 illustrates a cut-away view of an exemplary probe device.

FIG. 2 illustrates a cut-away view of an exemplary probe 200 which is similar in implementation and description to probe 100 shown in FIG. 1, above. Probe 200 includes a case 205 which includes a handle 210, a tip 215 having a cone 220 that holds electrical stimulator 225. Probe 200 also connects to a testing unit by cable 230. As shown in FIG. 2, probe 200 further includes a sliding core 235. Sliding core 235 allows contact between electrical stimulator 225 and electrical energy carried into probe 200 by cable 230 to be selectively applied to electrical stimulator 225 by actuating switch 240. In other words, sliding core 235 may apply spring force from spring 245 to switch 240 which allows electricity from cable 230 to flow to electrical stimulator 225. Spring 245 may be external to switch 240 or may be internal to switch 240. For example, a practitioner may apply probe 200 by pushing electrical stimulator 225 into a living body. Electrical stimulator 225 may cause sliding core 235 to engage internal switch 240, by spring pressure from spring 245, and allow electricity to flow from cable 230 to electrical stimulator 225. In this manner, electricity only flows to electrical stimulator 225 when pressure is applied to electrical stimulator 225 in tip 215 of probe 200. This configuration allows analysis of nerve injuries selectively without constant electrical power being applied through electrical stimulator 225 while probe 200 is in use.

Figure 3:
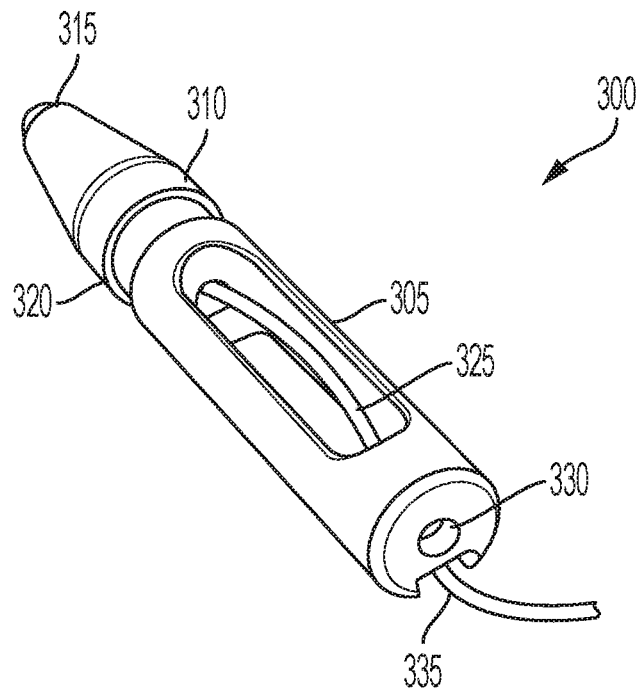
FIG. 3 illustrates an exemplary top section of an exemplary probe device.

FIG. 3 illustrates an exemplary tip section 300 of a probe, such as probe 100 shown and described above with respect to FIG. 1 and probe 200, shown and described above with respect to FIG. 2. As shown in FIG. 3, tip section 300 includes a body 305, a tip 310, and an electrical stimulator 315. Tip section 300 may include a safety catch 320 disposed between body 305 and tip 310 which connects tip section 300 to probe 200, as shown and described with respect to FIG. 2, and ensures that the sliding core, tip section 300, does not unintentionally separate from probe 200. Tip 300 may further include an interface with a switch 330 which may apply pressure to a rod associated with a switch, such as switch 240, shown in FIG. 2, which activates switch 240 when pressure is applied to electrical stimulator 315 and body 305 slides rearwardly to close switch 240. Tip 300 may further include a wire recess 335 which allows wire 325 to fit freely in body 305 as body 305 slides in probe 100 or probe 200, for example, without pulling or pushing on wire 325.

Figure 4:
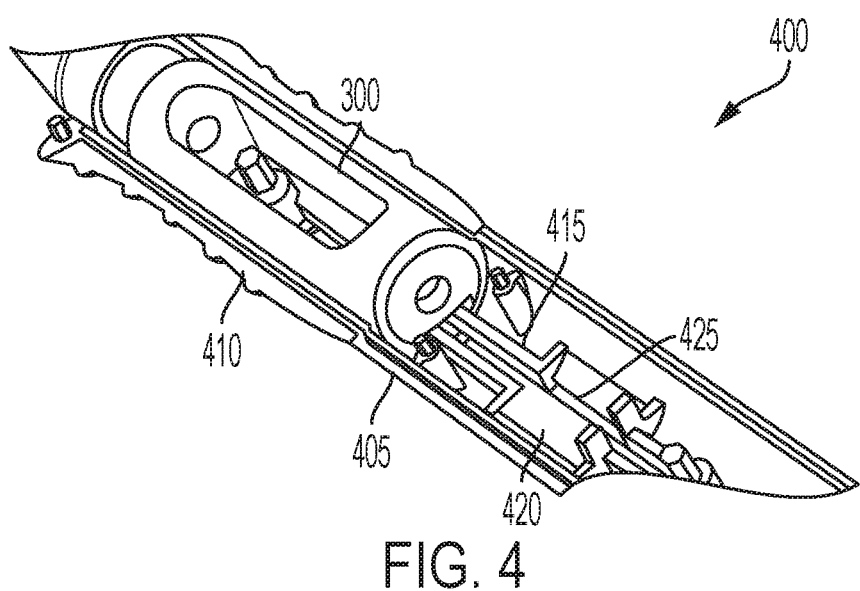
FIG. 4 illustrates a cut-away view of one section of the exemplary probe device.

FIG. 4 illustrates a cut-away view of a tip section 400 of a probe, such as probe 100 shown and described above with respect to FIG. 1 and probe 200 shown and described above with respect to FIG. 2. Tip section 400 includes a tip 300, which is similar in implementation and description to tip 300 shown in FIG. 4 assembled into tip section 400 of the probe. Tip section 400 further includes a body 405 and a handle 410, which have been previously discussed. As shown in FIG. 4, tip 300 may ride on runners 415 to slide back and forth as pressure is applied to an electrical stimulator disposed at a top of tip 300. A switch 420 may be installed in a pocket 425 such that switch 420 may be actuated by the sliding of tip 300 on runners 415. A wire, such as wire 325 shown in FIG. 3, may be disposed between runners 415 and within interface 335 to prevent wire 325 from being pushed or pulled by tip 300 sliding on runners 415. Runners 415 further guide tip 300 as it slides while also preventing tip 300 from rotating. Runners 415 further allow a wire to pass between them to a tip 300 around switch 420 and also leave probe 100/200 through cable 230.

Figure 5:
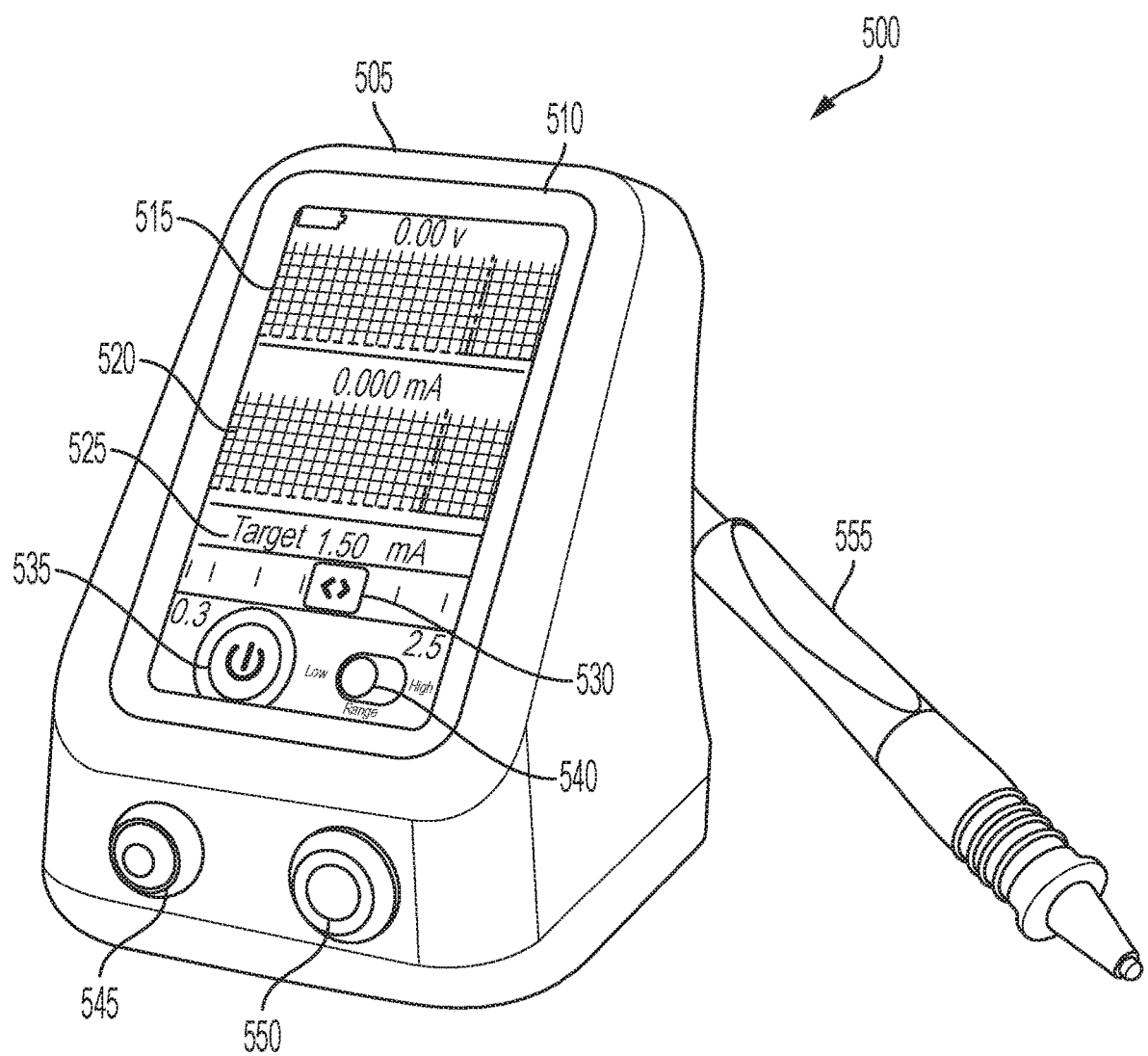
FIG. 5 illustrates an exemplary electrical nerve stimulator system.

FIG. 5 illustrates an exemplary electrical nerve stimulator system 500. Electrical nerve stimulator system 500 may be implemented with a housing 505 which includes an interactive display screen 510. Display screen 510 may be implemented as any type of screen, including a touch screen, LCD screens, LED screens, CRTV screens, or any other screen known in the art. Screen 510 may include a voltage indicator 515, an amperage indicator 520, an instructional indicator 525, a sliding element 530 for identifying a target current or voltage, a start/reset button 535, and a range button 540.

Voltage indicator 515 may provide a graph of voltage applied over time and a current voltage level of electrical nerve stimulator system 500. Amperage indicator 520 may provide a graph of current applied over time and a current amperage level of electrical nerve stimulator system 500. Instructional indicator 525 may provide a user with information about an intended level of current that is to be applied to a living body. Sliding element 530 may adjust a setting for the intended level of current that is to be applied to a living body. Power button 545 may cause electrical nerve stimulator system 500 to turn on or turn off, as desired. Range button 540 may allow a user to select between a high and low range of electrical current for application. Each of the foregoing indicators, elements, sliders, and buttons may be implemented as physical indicators, elements, or sliders, or buttons, or may be implemented as virtual indicators, elements, sliders, and buttons.

Electrical nerve stimulator system 500 further includes circuitry shown in Appendix A. For example, nerve stimulator system 500 may include a processor and memory, including transitory and non-transitory computer-readable storage media. Nerve stimulator system 500 may include software and hardware modules, sequences of instructions, routines, data structures, display interfaces, and other types of structures that execute computer operations. Further, hardware components may include a combination of Central Processing Units ("CPUs"), buses, volatile and non-volatile memory devices, storage units, non-transitory computer-readable media, data processors, processing devices, analog to digital converters, control devices transmitters, receivers, antennas, transceivers, input devices, output devices, network interface devices, and other types of components that are apparent to those skilled in the art. These hardware components within nerve stimulator system 500 may be used to execute the various identification and authentication methods, protocols, or events described herein. Nerve stimulator system 500 may be implemented as a computing device for a particular application such as voltage and amperage detection and nerve identification in a living body so long as the computing device itself includes one or more ports 550 for connecting an electrical pad and one or more ports for connecting probe 100 shown and described above with respect to FIG. 1 and probe 200 shown and described above with respect to FIG. 2, or, controlling a device which does contain one or more ports 550.

Further, nerve stimulator system 500 may further interface and communicate with another device, probe 100, probe 200, a remote cellular device, another display device, another computer device, or any other device, as desired, using a communication protocol, which may include a wired ethernet connection or a wireless 802.11x connection. Communication protocols may be any suitable communication protocol known in the art and are not limited to the exemplary implementations described herein. For example, any of communication protocol 125*a*, 125*b*, and 125*c* may be implemented using Wi-Fi, Bluetooth, ZigBee, Z-Wave, RF4CE, Ethernet, telephone line, cellular channels, or others that operate in accordance with protocols defined in IEEE (Institute of Electrical and Electronics Engineers) 802.11, 801.11a, 801.11b, 801.11e, 802.11g, 802.11h, 802.11i, 802.11n, 802.16, 802.16d, 802.16e, or 802.16m using any network type including a wide-area network ("WAN"), a local-area network ("LAN"), a 2G network, a 3G network, a 4G network, a Worldwide Interoperability for Microwave Access (WiMAX) network, a Long Term Evolution (LTE) network, Code-Division Multiple Access (CDMA) network, Wideband CDMA (WCDMA) network, any type of satellite or cellular network, NFC communication protocols, or any other appropriate protocol to facilitate communication nerve stimulator system 500 and other devices, as desired.

Nerve stimulator system 500 may further include one or more ports 550 for connecting an electrical pad to a living body and one or more ports 550 for connecting probe 555 to electrical nerve stimulator system 500. Probe 555 may be similar in implementation and description to probe 100 shown and described above with respect to FIG. 1 and probe 200 shown and described above with respect to FIG. 2. Electrical nerve stimulator system 500 may include a battery and or receive power from a standard electrical outlet.

In practice, a doctor, for example, may apply an electrical pad to a living body in a location along a spinal column. The doctor may then apply probe 555 to, for example, a location of pain in the living body. As the pressure is applied to a tip of probe 555, electrical power will be conducted from the electrical pad, through the living body, and into probe 555. Display 510 may indicate that an injured nerve has been located by an increase in current and/or voltage displayed in voltage indicator 515 and amperage indicator 520. As the injured nerve is located, the circuit is completed by application of probe 555, which causes the voltage and current to spike on display 510. If no voltage or current spike is noted during probing, it is likely that a patient is claiming injury and pain for other reasons, such as to obtain medication. When a voltage and/or current spike is detected, electricity may be applied to the nerve to deaden the nerve for a substantial period of time, such as up to several years, alleviating pain caused by that nerve.

Figure 6:
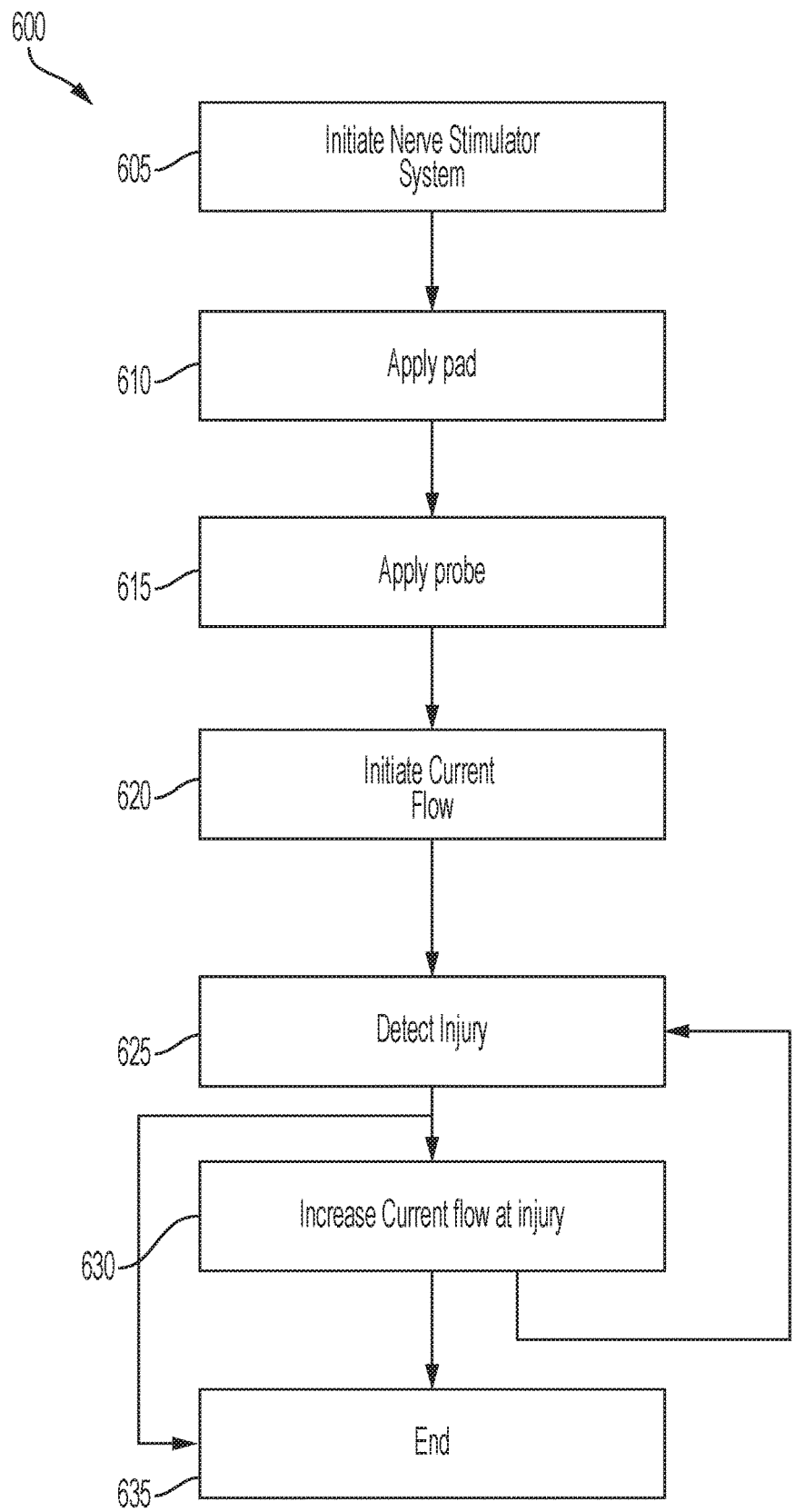
FIG. 6 illustrates an exemplary method for treating a nerve injury or nerve impingement in a living body.

FIG. 6 illustrates an exemplary method 600 for treating a nerve injury or nerve impingement in a living body. Method 600 begins by initiating an electrical nerve stimulator system, such as electrical nerve stimulator system 500 shown in FIG. 5 and discussed above. Initiating electrical nerve stimulator system may include one or more of turning on nerve stimulator system 500, connecting an electrical pad to nerve stimulator system 500, connecting a probe to nerve stimulator system 500, initializing electronic components, interacting with one or more elements, buttons, sliders, or other interface elements on a display, or other boot up procedure. In one embodiment, once electrical nerve stimulator system 500 has been initiated, nerve stimulator system 500 may begin, in one example, to output a pulse width modulated output at a 50% duty cycle at 3 hz, although when a probe, such as probe 555 in FIG. 5, is not activated, the output of nerve stimulator system 500 is not provided to an electrical stimulator in probe 555. Other pulse width modulated outputs are possible as determined by an operator of nerve stimulator system 500. At any time, a user may stop the output by a stop button or may adjust a slider to reset a target current to be applied to a patient.

At step 610, a practitioner may apply an electrical pad to the skin of a living body. The electrical pad may complete the circuit for the probe as the probe is applied to the living body in step 615 and current is applied to one or more nerves within the living body. At step 615, probe 555 is activated by pressing a tip of probe 555 into a living body in a manner that ensures electrical conductivity but without injuring the living body. Probe 555 is transcutaneous, which means that probe 555 is intended to be exvivo during use and not intervivo on the living body. The skin is not penetrated by probe 555. Although, it is contemplated that in the hands of a skilled surgeon, probe 555 may be used in an intervivo manner during a surgical procedure. At step 620, the tip of probe 555 is applied to the living body, the output voltage from nerve stimulator system 500 is increased while the applied current is monitored closely via a display screen, such as display screen 510 shown in FIG. 5. A digital potentiometer may be automatically adjusted in a voltage divider to apply the target current at an appropriate voltage, according to Ohm's Law, to ensure that an intended output voltage is conveyed to probe 555. A processor may constantly monitor output voltage and current to ensure that the applied current is within an acceptable range and may include a software based current limiter. At the same time, a resistor may be included in the circuit to set a maximum current limit with discrete components, providing a redundant current limiter for safety.

At step 625, probe 555 may detect a nerve injury location in a living body by detecting a spike in voltage or current output of nerve stimulator system 500. As probe 555 is moved to different locations on the living body, an analog to digital converter in the processor adjusts the output voltage to increase or decrease to reach the target current specified on display screen 510. Once a nerve injury location is identified at step 625, nerve stimulator system 500 may increase the current flow at the nerve injury location at step 630. For minor pain, low currents may interfere with signals transmitted by the nerve to the brain of the living body and have a pain reducing effect for days, weeks, or months. For more severe pain, higher currents may be used to deaden the nerve for months or years to alleviate pain. In some cases, surgeons have severed nerves to reduce back pain. Nerve stimulator system 500 provides the same benefit with no need for intervivo surgery, increasing recovery time and minimizing possibility for unintended damage during very delicate surgery.

It may be that no nerve injury is detected in step 625 of method 600. However, such an indication may be caused by a patient feigning pain in order to obtain prescription medication. In this case, method 600 may end at step 635. In this case, detecting an injury may mean detecting an indication of pain medication, opioid, or other drug addiction. Once step 630 is completed, method 600 may continue again at step 625 to locate other sources of pain or, method 600 may end at step 635.

Figure 7:
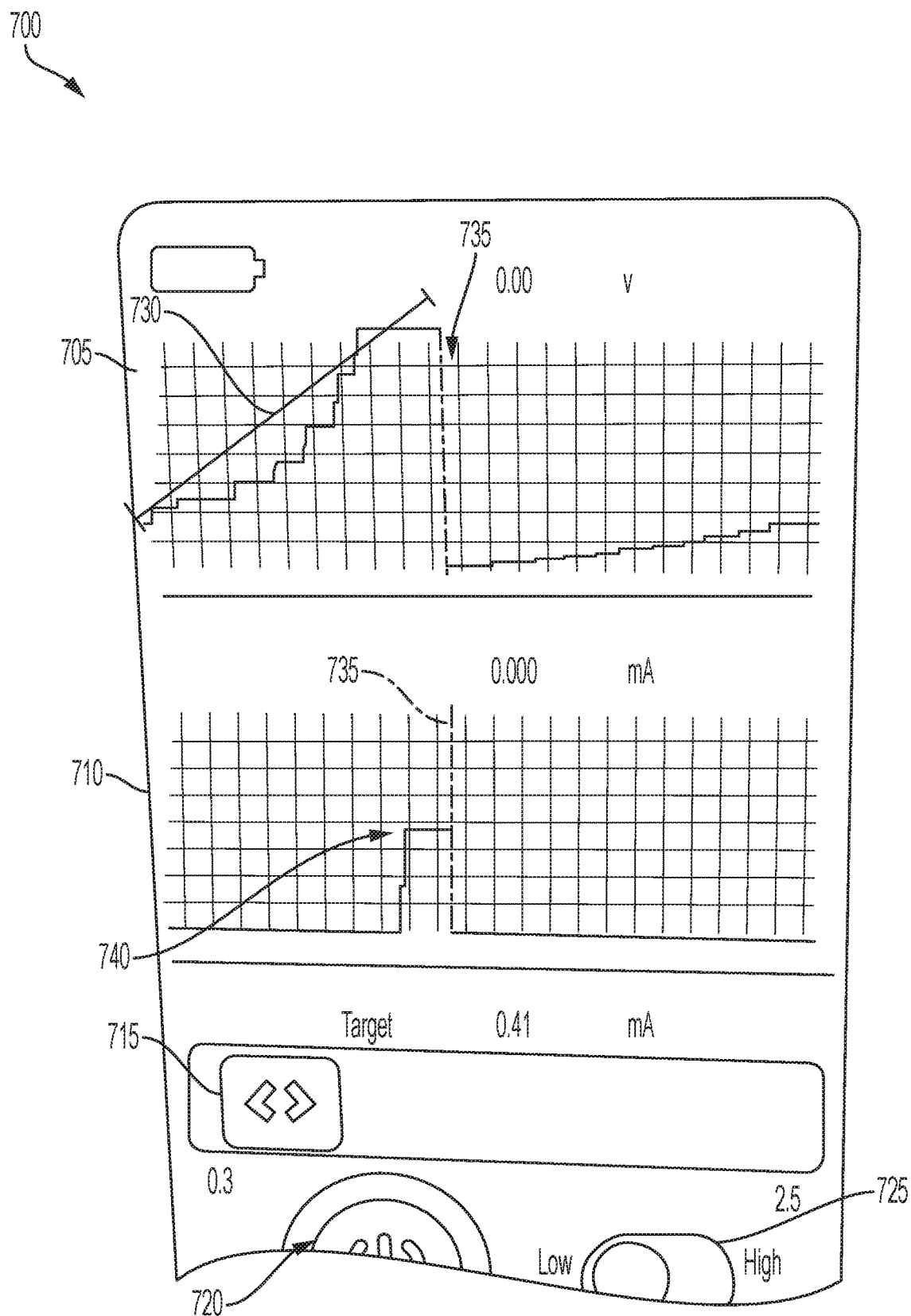
FIG. 7 illustrates an exemplary interface illustrating a pain detection event.

FIG. 7 illustrates a pain detection event in a graphical user interface 700. As shown in FIG. 7, graphical user interface 700 may be implemented on display screen 510, shown and described above with respect to FIG. 5. Graphical user interface includes a voltage indicator 705, an amperage indicator 710, a sliding element 715 for identifying a target current or voltage, a start/reset button 720, and a range button 725. As shown in FIG. 7, and in one example of detecting a nerve injury in step 625 of method 600, a voltage increase 730 is occurring prior to and up to time 735 in voltage indicator 705. In another example of detecting a nerve injury in step 625 of method 600A corresponding increase of amperage 740 is occurring prior to and up to time 735 in amperage indicator 710. The pain detection event in graphical user interface 700 was obtained by testing a subject's L4 spinal disc with a probe, such as probe 100 or probe 200 shown in FIGS. 1 and 2 respectively, with an electrode patch on a foot of the subject. The voltage increase 730 and amperage increase 740 indicate that the subject is feeling pain in her foot but the pain is actually being generated at the L4 spinal disc and not in the subject's foot. Graphical user interface 700 may allow an operator to switch from a high mode to a low mode via sliding element 715 to adjust the sensitivity of the overall device. A high mode (selected by range button 540) may provide an increased voltage or current than what may be provided in a low mode which allows for more sensitive detection of an injury, for example.

One overarching benefit of the electrical nerve stimulator described herein is that it provides an objective measurement of pain actually occurring. For example, as shown in graphical user interface, a 0.41 mA current shows that the pain experienced by the subject is constant and chronic. In this manner it is possible to objectively demonstrate that a patient or subject is objectively experiencing pain and provides an objective measurement for how much pain is experienced by the patient or subject. When an operator, a doctor for example, can objectively identify that pain is occurring and the relative amount of pain, a doctor can more accurately assess treatment strategies for that pain. Alternatively, when an operator can see that no pain objectively exists in the area complained of by the patient or subject, the operator may identify that a patient or subject is feigning pain in order to receive pain medication. An operator may treat patients and subjects in both scenarios accordingly by applying an electrical pulse to the nerve using probe 100/200 which numbs the nerve for a period of time. The operator may also use alternative treatments, such as pain medication, addiction counseling, or other treatments depending on the operator's professional judgement.

The foregoing description has been presented for purposes of illustration. It is not exhaustive and does not limit the disclosure to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims, if any.

Other embodiments will be apparent to those skilled in the art from consideration of the specification and practice of the disclosure disclosed herein. It is intended that the specification and examples be considered as exemplary only, with a true scope and spirit of the invention being indicated by the claims, if any.

What is claimed is:

1. A probe, comprising:
   an internal switch which is operable by a sliding core to initiate electrical conductivity to a tip of the probe, wherein the sliding core slides over and contacts one or more runners within the probe, and an electrical stimulator disposed at a tip of the probe which is selectively electrified by applying the tip of the probe to skin which causes the sliding core to interface with the switch.

2. The probe of claim 1, wherein the probe is contained within a casing.

3. The probe of claim 1, wherein the electrical stimulator is made from copper.

4. The probe of claim 1, further comprising a catch disposed at a tip end of the probe.

5. The probe of claim 1, wherein the internal switch initiates electrical conductivity when pressure is applied to the tip of the probe.

6. The probe of claim 5, wherein the internal switch includes a spring.

7. The probe of claim 6, wherein the pressure applied to the tip of the probe causes the sliding core to slide into the probe and initiates electrical conductivity to the tip of the probe.

8. The probe of claim 1, wherein a wire is disposed between the runners.

9. The probe of claim 1, wherein the probe is connected to a cable which provides current at a particular voltage to the electrical stimulator.

10. The probe of claim 9, wherein the provided current and particular voltage are adjustable.

* * * * *